United States Patent
El-kalliny

(10) Patent No.: US 11,322,264 B2
(45) Date of Patent: May 3, 2022

(54) SYSTEMS AND METHODS FOR HUMAN-AUGMENTED COMMUNICATIONS

(71) Applicant: DNAFeed Inc., San Diego, CA (US)

(72) Inventor: Ahmed El-kalliny, San Diego, CA (US)

(73) Assignee: DNAFeed Inc., San Diego, CA (US)

( * ) Notice: Subject to any disclaimer, the term of this patent is extended or adjusted under 35 U.S.C. 154(b) by 529 days.

(21) Appl. No.: 16/384,823

(22) Filed: Apr. 15, 2019

(65) Prior Publication Data
US 2019/0326022 A1    Oct. 24, 2019

Related U.S. Application Data

(60) Provisional application No. 62/661,095, filed on Apr. 23, 2018.

(51) Int. Cl.
| | |
|---|---|
| G16H 80/00 | (2018.01) |
| G06F 16/9032 | (2019.01) |
| G06K 9/62 | (2022.01) |
| G16H 20/10 | (2018.01) |
| G16H 50/30 | (2018.01) |
| H04L 51/02 | (2022.01) |
| H04L 51/18 | (2022.01) |
| H04L 51/10 | (2022.01) |
| G16H 10/20 | (2018.01) |
| H04L 51/046 | (2022.01) |

(52) U.S. Cl.
CPC ........ *G16H 80/00* (2018.01); *G06F 16/90332* (2019.01); *G06K 9/6254* (2013.01); *G16H 20/10* (2018.01); *G16H 50/30* (2018.01); *H04L 51/02* (2013.01); *H04L 51/18* (2013.01)

(58) Field of Classification Search
CPC ........ G16H 80/00; G16H 50/30; G16H 20/10; G06F 16/90332; G06K 9/6254; H04L 51/02; H04L 51/18; H04L 12/58
USPC ........................................................ 706/45
See application file for complete search history.

(56) References Cited

U.S. PATENT DOCUMENTS

| | | |
|---|---|---|
| 8,553,065 B2 | 10/2013 | Gannu et al. |
| 8,996,639 B1 | 3/2015 | Faaborg et al. |
| 9,740,677 B2 | 8/2017 | Kim et al. |
| 9,741,259 B2 * | 8/2017 | Mahmud .................. G09B 7/00 |
| 9,756,091 B1 | 9/2017 | Davies |
| 9,785,715 B1 | 10/2017 | Busey et al. |

(Continued)

*Primary Examiner* — Umar Cheema
*Assistant Examiner* — Tony Williams
(74) *Attorney, Agent, or Firm* — American Patent Agency PC; Daniar Hussain

(57) ABSTRACT

The present disclosure is generally directed to the field of human-augmentation using computing devices and techniques. In particular, a computer-implemented method may include: (1) identifying, via a message identification component, at least one message associated with a message exchange platform, the message including a query; (2) transmitting, via a communication component, the message to one or more users at respective user devices; (3) receiving, via a recommendation component, responses to the query from the respective user devices; (4) determining, via a scoring component, respective scores of the responses; and (5) selecting, via the scoring component, at least one response having a score exceeding a predetermined threshold. Various other methods, systems, devices, and computer-readable media are also disclosed.

19 Claims, 11 Drawing Sheets

(56) References Cited

U.S. PATENT DOCUMENTS

| | | | |
|---|---|---|---|
| 2014/0288969 A1* | 9/2014 | Goltra | G16B 20/20 |
| | | | 705/3 |
| 2017/0048170 A1* | 2/2017 | Smullen | H04L 67/02 |
| 2017/0180276 A1 | 6/2017 | Gershony et al. | |
| 2017/0180294 A1 | 6/2017 | Milligan et al. | |
| 2017/0337199 A1* | 11/2017 | Kogan | H04W 4/14 |
| 2017/0364593 A1* | 12/2017 | Busey | G06N 20/00 |
| 2018/0024991 A1* | 1/2018 | Baldwin | H04L 51/36 |
| | | | 704/9 |

\* cited by examiner

FIG. 6B

SYSTEMS AND METHODS FOR HUMAN-AUGMENTED COMMUNICATIONS

REFERENCE TO PROVISIONAL APPLICATION

This application is related to and claims priority from provisional application with U.S. Ser. No. 62/661,095, filed on Apr. 23, 2018, and entitled "SYSTEM AND METHOD FOR PROVIDING HUMAN-GENERATED AUGMENTED DATA FOR MESSAGING APPLICATIONS," the entire disclosure of which is hereby incorporated by reference in its entirety herein.

NOTICE OF COPYRIGHTS AND TRADE DRESS

A portion of the disclosure of this patent document may contain material which is subject to copyright protection. This patent document may show and/or describe matter which is or may become trade dress of the owner. The copyright and trade dress owner has no objection to the facsimile reproduction by anyone of the patent disclosure as it appears in the U.S. Patent and Trademark Office files or records, but otherwise reserves all copyright and trade dress rights whatsoever.

FIELD OF THE DISCLOSURE

Embodiments of the present invention are generally directed to systems and methods for human-augmented communications.

BACKGROUND OF THE INVENTION

Communications platforms such as text and chat messaging may provide interactions between consumers and businesses. Such communications platforms may enable point-to-point communications between a sender and a receiver as well as multicast communications from one sender to many receivers. However, there exists a need for businesses to provide higher-quality, higher-efficiency, and higher-consistency communications to their customers. It is against this background that the present disclosure was developed.

BRIEF SUMMARY OF THE INVENTION

The following presents a summary to provide a basic understanding of one or more embodiments of the disclosure. This summary is not intended to identify key or critical elements, or to delineate any scope of particular embodiments or any scope of the claims. Its sole purpose is to present concepts in a simplified form as a prelude to the more detailed description that is presented later. In one or more embodiments described herein, systems, computer-implemented methods, apparatuses and/or computer program products that provide a human-augmented and collaborative messaging platform for users communicating over a network. Such users may be located in different geographical areas and may simultaneously be engaged in communication over the network. Further, the users may have visibility of a given communications session, and thus may augment each other's responses accordingly via the messaging platform. In some cases, the users may have particular licenses or other forms of authorization to communicate to other users, and the messaging platform or other systems may examine and authorize users based on the validity of their credentials. Moreover, artificial intelligence (AI) may be used to enhance the generation of responses to queries between users on the collaborative messaging platform.

In general, one innovative aspect of the subject matter described herein can be embodied in methods that include the actions of: identifying, via a message identification component, at least one message associated with a message exchange platform, the message including a query; transmitting, via a communication component, the message to one or more users at respective user devices; receiving, via a recommendation component, responses to the query from the respective user devices; determining, via a scoring component, respective scores of the responses; and selecting, via the scoring component, at least one response having a score exceeding a predetermined threshold. The message identification component, communication component, recommendation component, and the scoring component are further described at least in connection with FIG. 5, below.

Other embodiments of this aspect include corresponding systems, apparatus, and computer programs, configured to perform the actions of the methods, encoded on computer storage devices.

These and other embodiments can each optionally include one or more of the following features. In particular, embodiments may include the method further determining, via the recommendation component, at least one AI-based response to the query using an AI-based technique. The method may include transmitting, via the communication component, the AI-based response to the users at the respective user devices, and receiving, via the recommendation component, the responses to the query from the respective user devices based on the AI-based response. The method may also include identifying, via the message identification component, from a database of previously generated responses associated with the query, at least one previously generated response and inputting the previously generated response to the AI-based technique. Such previously generated responses may thereby be used to train the AI-based technique (e.g., a supervised or semi-supervised machine-learning algorithm).

Particular embodiments of the subject matter described herein can be implemented so as to realize one or more of the following advantages. Reducing the amount of information transmitted over wired and/or wireless networks. Increasing the efficiency of communications by providing AI-generated responses to user queries for selection and/or augmentation by other users. Providing increased accuracy of responses (e.g., responses indicative of diagnoses and treatments in the medical field) by providing a collaborative platform for users to engage in communication over the message exchange platform. Reducing the amount of onboard computation at user devices by offloading particular AI operations and or computer search queries onto third-party servers, thereby reducing the computational load on user devices. Providing a historical repository of communications that may increase the efficiency of both user-generated and/or AI-generated responses to queries.

Features from any of the embodiments described herein may be used in combination with one another in accordance with the general principles described herein. The details of one or more embodiments of the subject matter described herein are set forth in the accompanying drawings and the description below. Other features, aspects, and advantages of the subject matter will become apparent from the description, the drawings, and the claims.

BRIEF DESCRIPTION OF THE DRAWINGS

Figure 1:
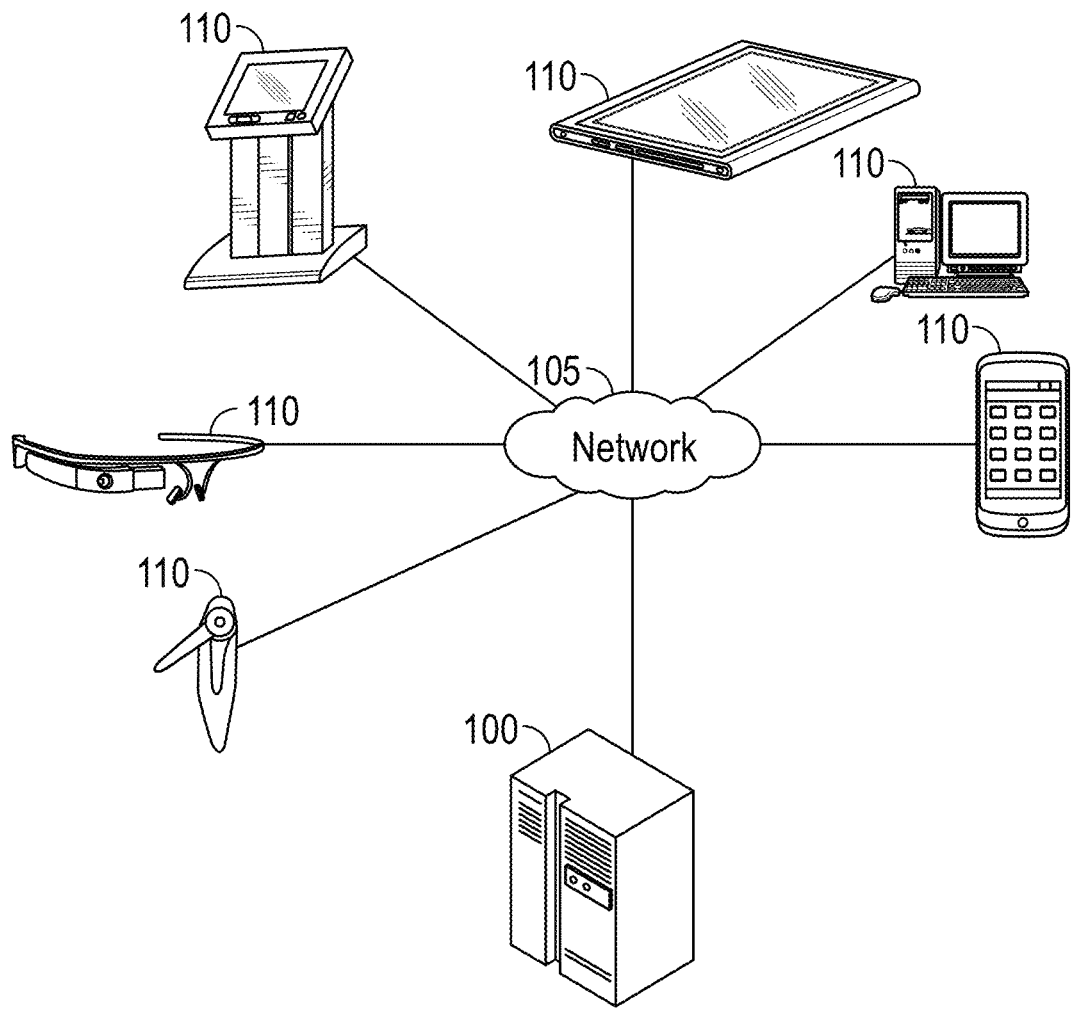

Having thus described the disclosure in general terms, reference will now be made to the accompanying drawings, which are not necessarily drawn to scale, and wherein:

FIG. 1 is an overview of a system that can be used to practice embodiments of the present disclosure.

Figure 2:
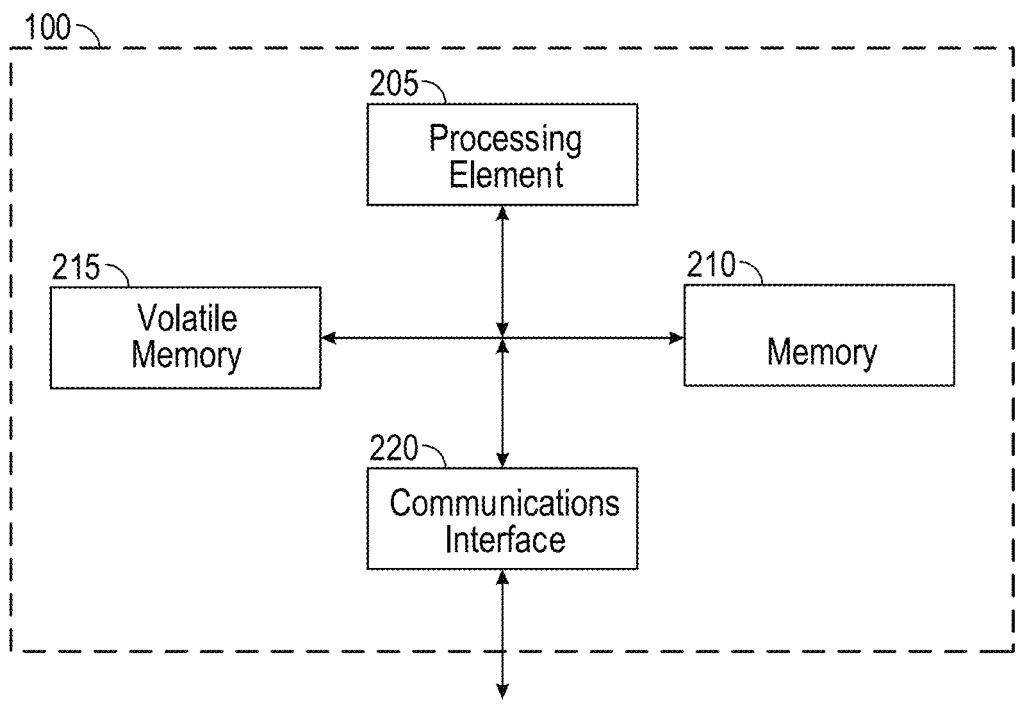

FIG. 2 is an exemplary schematic diagram of a management computing entity according to one embodiment of the present disclosure.

Figure 3:
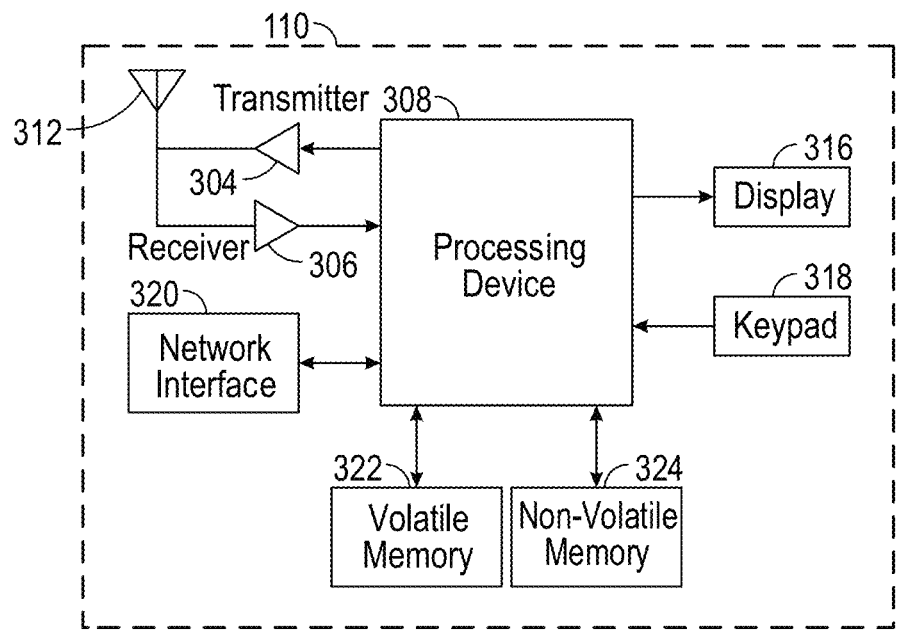

FIG. 3 is an exemplary schematic diagram of a user computing entity according to one embodiment of the present disclosure.

Figure 4:
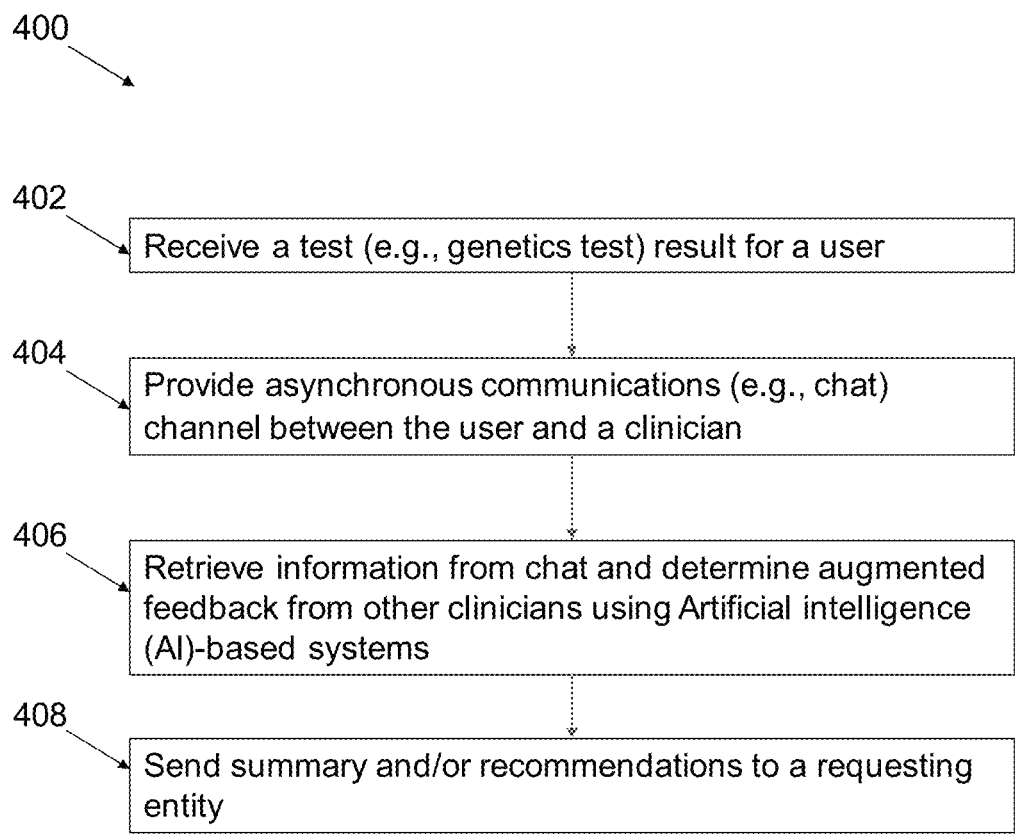

FIG. 4 illustrates a flow diagram of an example, non-limiting method that can facilitate human-augmented messaging, in accordance with example embodiments of the disclosure.

Figure 5:
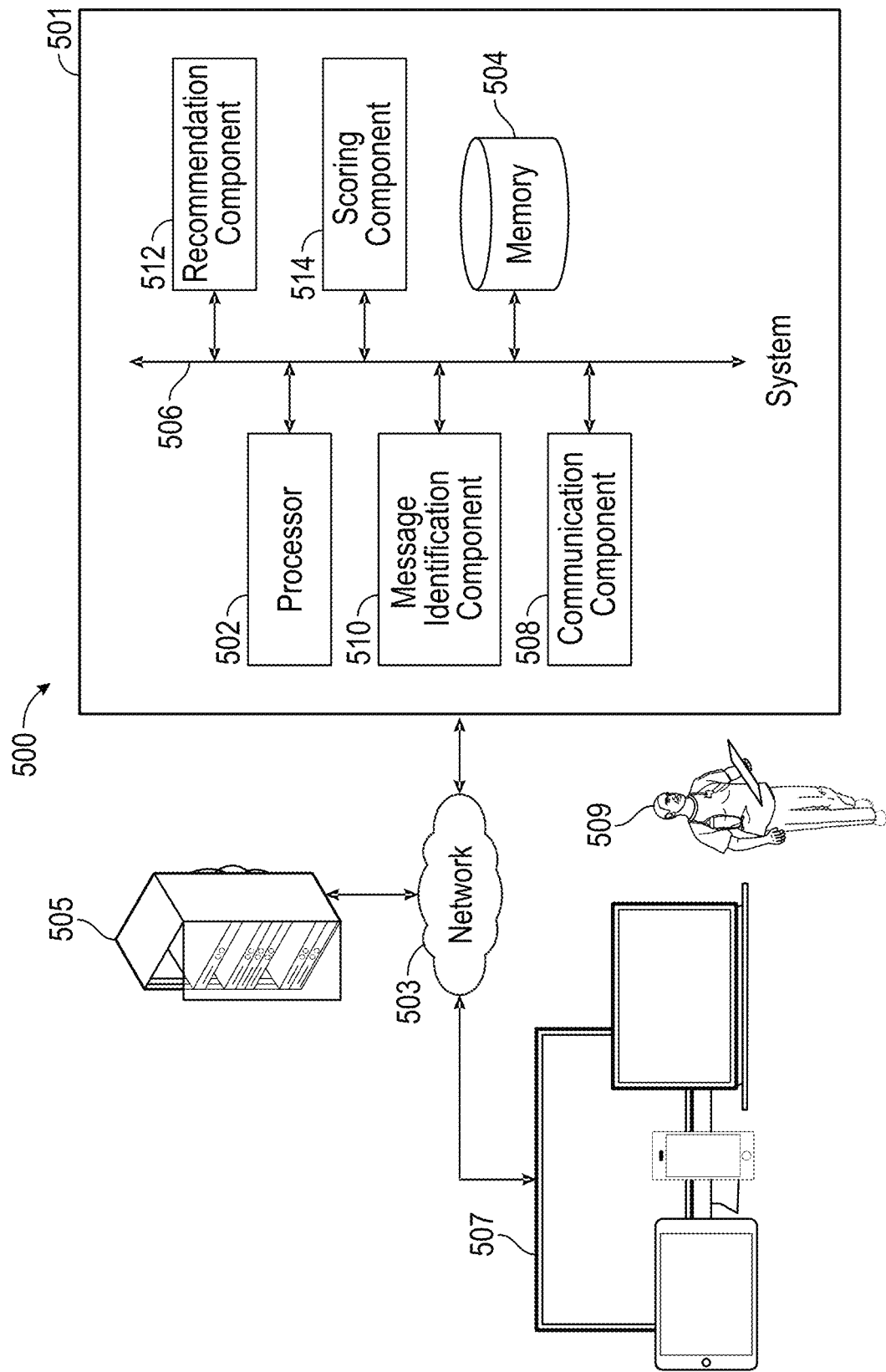

FIG. 5 illustrates a block diagram of an example, non-limiting system for providing a human-augmented communications platform, in accordance with example embodiments of the disclosure.

FIGS. 6A, 6B, 6C, and 6D illustrate diagrams various aspects of a chat application used by the disclosed systems to provide human-augmented communications, in accordance with example embodiments of the disclosure.

Figure 7:
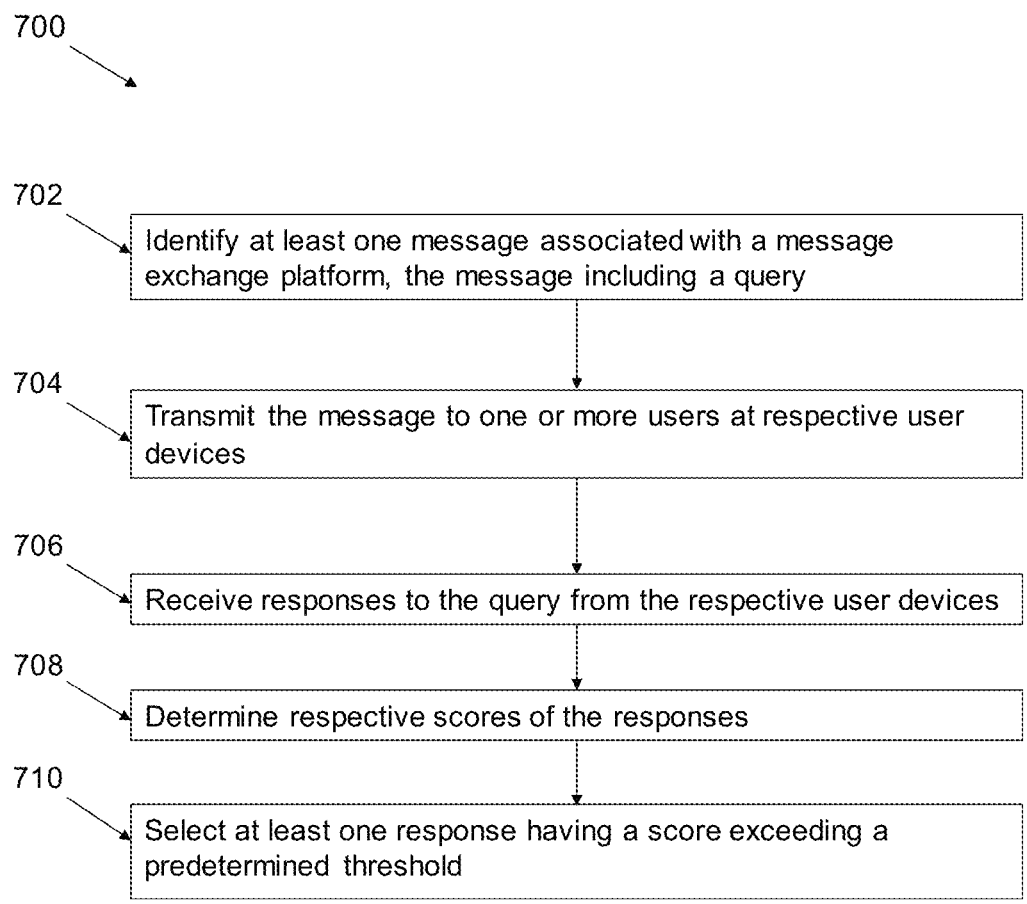

FIG. 7 illustrates an exemplary method for performing the operations described herein, in accordance with example embodiments of the disclosure.

Figure 8:
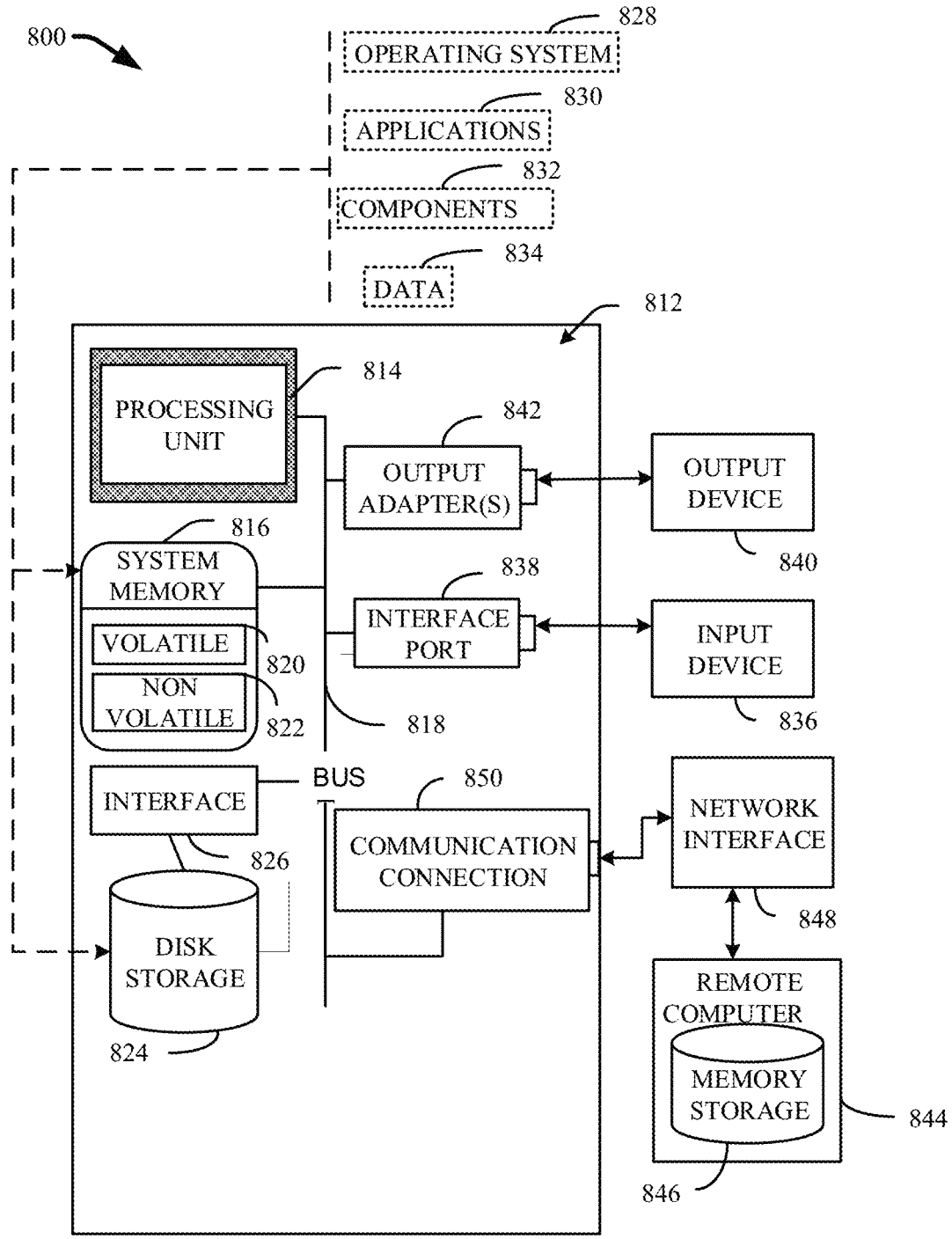

FIG. 8 illustrates a block diagram of an example, non-limiting operating environment in which one or more embodiments described herein can be facilitated.

Figure 9:
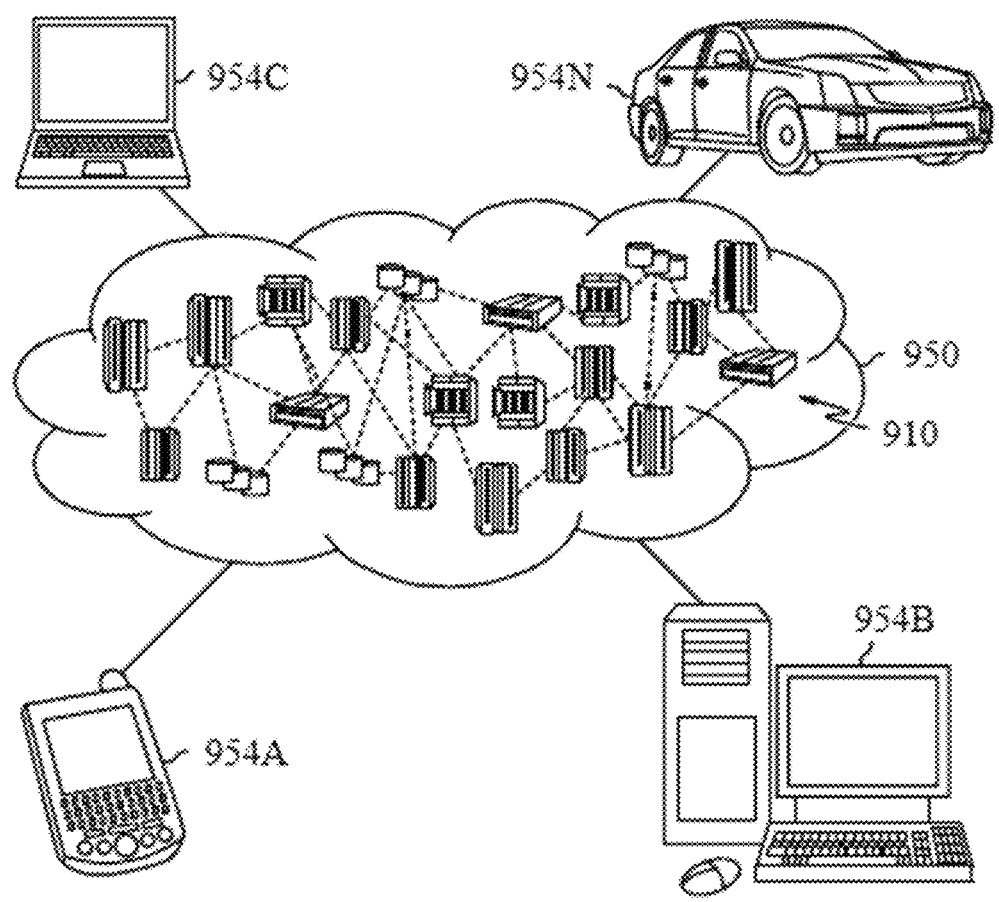

FIG. 9 depicts a cloud computing environment in accordance with one or more embodiments described herein.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the present disclosure covers all modifications, equivalents, and alternatives falling within the scope of the appended claims.

DETAILED DESCRIPTION OF VARIOUS EMBODIMENTS

Various embodiments of the present disclosure now will be described more fully hereinafter with reference to the accompanying drawings, in which some, but not all embodiments of the disclosures are shown. Indeed, these disclosures may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. Computer Program Products, Methods, and Computing Entities

Embodiments of the present disclosure may be implemented in various ways, including as computer program products that comprise articles of manufacture. A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of an apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

FIG. 1 provides an illustration of an exemplary embodiment of the present disclosure. As shown in FIG. 1, this particular embodiment may include one or more management computing entities 100, one or more networks 105, and one or more user computing entities 110. Each of these components, entities, devices, systems, and similar words used herein interchangeably may be in direct or indirect communication with, for example, one another over the same or different wired or wireless networks. Additionally, while FIG. 1 illustrates the various system entities as separate, standalone entities, the various embodiments are not limited to this particular architecture.

1. Exemplary Management Computing Entity

FIG. 2 provides a schematic of a management computing entity 100 according to one embodiment of the present disclosure. In general, the terms computing entity, computer, entity, device, system, and/or similar words used herein interchangeably may refer to, for example, one or more computers, computing entities, desktop computers, mobile phones, tablets, phablets, notebooks, laptops, distributed systems, gaming consoles (e.g., Xbox, Play Station, Wii), watches, glasses, iBeacons, proximity beacons, key fobs, radio frequency identification (RFID) tags, ear pieces, scanners, televisions, dongles, cameras, wristbands, wearable items/devices, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the management computing entity 100 may also include one or more communications interfaces 220 for communicating with various computing entities, such as by communicating data, content, information, and/or similar terms used herein interchangeably that can be transmitted, received, operated on, processed, displayed, stored, and/or the like. For instance, the carrier computing entity 100 may communicate with user computing entities 110 and/or a variety of other computing entities.

As shown in FIG. 2, in one embodiment, the carrier computing entity 100 may include or be in communication with one or more processing elements 205 (also referred to as processors, processing circuitry, and/or similar terms used herein interchangeably) that communicate with other elements within the management computing entity 100 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In one embodiment, the management computing entity 100 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the management computing entity 100 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the management computing entity 100 with the assistance of the processing element 205 and operating system.

As indicated, in one embodiment, the management computing entity 100 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the carrier computing entity 100 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol.

Although not shown, the management computing entity 100 may include or be in communication with one or more input elements, such as a keyboard input, a mouse input, a touch screen/display input, motion input, movement input, audio input, pointing device input, joystick input, keypad input, and/or the like. The carrier computing entity 100 may also include or be in communication with one or more output elements (not shown), such as audio output, video output, screen/display output, motion output, movement output, and/or the like.

As will be appreciated, one or more of the management computing entity's 100 components may be located remotely from other management computing entity 100 components, such as in a distributed system. Furthermore, one or more of the components may be combined and additional components performing functions described herein may be included in the management computing entity 100. Thus, the management computing entity 100 can be adapted to accommodate a variety of needs and circumstances. As will be recognized, these architectures and descriptions are provided for exemplary purposes only and are not limiting to the various embodiments.

2. Exemplary User Computing Entity

A user may be an individual, a family, a company, an organization, an entity, a department within an organization, a representative of an organization and/or person, and/or the like. In one example, users may be carrier personnel, consignors/shippers, consignees/recipients, and/or the like. For instance, a user may operate a user computing entity 110 that includes one or more components that are functionally similar to those of the carrier computing entity 100. FIG. 3 provides an illustrative schematic representative of a user computing entity 110 that can be used in conjunction with embodiments of the present disclosure. In general, the terms device, system, computing entity, entity, and/or similar words used herein interchangeably may refer to, for example, one or more computers, computing entities, desktops, mobile phones, tablets, phablets, notebooks, laptops, distributed systems, gaming consoles (e.g., Xbox, Play Station, Wii), watches, glasses, key fobs, radio frequency identification (RFID) tags, ear pieces, scanners, cameras, wristbands, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. User computing entities 110 can be operated by various parties. As shown in FIG. 3, the user computing entity 110 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, respectively.

The signals provided to and received from the transmitter 304 and the receiver 306, respectively, may include signaling information in accordance with air interface standards of applicable wireless systems. In this regard, the user computing entity 110 may be capable of operating with one or more air interface standards, communication protocols, modulation types, and access types. More particularly, the user computing entity 110 may operate in accordance with any of a number of wireless communication standards and protocols, such as those described above with regard to the carrier computing entity 100. In a particular embodiment, the user computing entity 110 may operate in accordance with multiple wireless communication standards and protocols, such as UMTS, CDMA2000, 1×RTT, WCDMA, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the user computing entity 110 may operate in accordance with multiple wired communication standards and protocols, such as those described above with regard to the carrier computing entity 100 via a network interface 320.

Via these communication standards and protocols, the user computing entity 110 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 110 can also download changes, add-ons, and updates, for instance, to its firmware, software (e.g., including executable instructions, applications, program modules), and operating system.

According to one embodiment, the user computing entity 110 may include location determining aspects, devices, modules, functionalities, and/or similar words used herein interchangeably. For example, the user computing entity 110 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites. The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information can be determined by triangulating the user computing entity's 110 position in connection with a variety of other systems, including cellular towers, Wi-Fi access points, and/or the like. Similarly, the user computing entity 110 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The user computing entity 110 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the user computing entity 110 to interact with and/or cause display of information from the carrier computing entity 100, as described herein. The user input interface can comprise any of a number of devices or interfaces allowing the user computing entity 110 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the user computing entity 110 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The user computing entity 110 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the user computing entity 110. As indicated, this may include a user application that is resident on the entity or accessible through a browser or other user interface for communicating with the management computing entity 100 and/or various other computing entities.

In another embodiment, the user computing entity 110 may include one or more components or functionality that are the same or similar to those of the carrier computing entity 100, as described in greater detail above. As will be recognized, these architectures and descriptions are provided for exemplary purposes only and are not limiting to the various embodiments.

III. Exemplary System Operation

As described above, the management computing entity 100 and/or user computing entity 110 may be configured to coordinate the operations associated with messaging by users over a network, as will be detailed further below.

As used herein, "human-to-human augmentation" and/or "human augmentation" may refer to systems and methods that allow individuals to supplement each other's communications using technology. In particular, the management computing entity 100 may offer a message exchange platform that allows multiple users to oversee a conversation and contribute to the conversation, thereby enhancing the depth and scope of responses than would be provided by a single user.

As used herein, a "message exchange platform" may refer to a computer-implemented tool that enables users to exchange messages over a network to enable personalized interactions between entities such between users (e.g., patients and licensed clinicians).

As used herein, a "message" may refer to a discrete unit of communication intended by the source for consumption by some recipient or group of recipients. Messages may include communications between the users of computer systems that are delivered by those computer systems.

As used herein, a "query" may refer to a form of questioning in a line of inquiry. The query may include one or more questions that include a request for information. Further, as used herein, a "response" may refer to an answer to the query and may include textual information that provides the answer.

As used herein, a "score" may refer to a numerical representation of a relative adequacy of a given response. In particular, the score may be generated using AI-based techniques (to be detailed herein) for responses to queries provided by various entities.

As used herein, a "user-generated response" may refer to a response that is generated by a human user.

As used herein, a "user-augmented response" may refer to a response that is enhanced or otherwise supplemented by at least one other user or an AI-based technique.

As used herein, an "AI-based response" may refer to a response that is generated at least partially using a computer-implemented algorithm, such as a with a machine learning algorithm.

As used herein, a "predetermined response" may refer to a response that has been previously generated to a given query or to a related query. As such, a predetermined response may represent a relatively quick and convenient mechanism for a user (e.g., a licensed physician) to provide a response to a user (e.g., a patient). In the message exchange platform, the users may insert a predetermined response triggered by keystrokes or from application-based menus, rather than typing the same answer repeatedly or pasting from an external resource.

As used herein, a "keyword" may refer to a term in information retrieval that serves to captures the spirit of the topic of a conversation in a chatting session. Keywords may also be used interchangeably with the following: index term, subject term, subject heading, or descriptor. In some examples, keywords may include tags which can be assigned by non-experts or with computer-based techniques. Keywords may include a word, phrase, or alphanumerical term. They may be created by analyzing the messages either manually with subject indexing or automatically with automatic indexing or more sophisticated methods of keyword extraction. Keywords can either come from a controlled vocabulary or be freely assigned.

As used herein, an "entity" may refer to any suitable organization that has personnel that are authorized to engage in communications with end-users (e.g., patients) on the message exchange platform. In the context of the examples provided in this disclosure, an entity may include various medical institutions including, but not limited to, trauma centers, rehabilitation hospitals, children's hospitals, seniors' hospitals, and hospitals for dealing with specific medical needs such as psychiatric treatment and certain disease categories. It is to be understood that while the entities primarily referenced in the various examples in this disclosure relates to the healthcare field, entities may also include organizations associated with other industries including, but not limited to, engineering, information technology (IT), aviation, retail, and/or the like.

Moreover, a "user" as used herein may refer to any suitable personnel associated with an entity. In the context of the examples provided in this disclosure, the user may refer to a health professional that may operate within all branches of health care, including medicine, surgery, dentistry, midwifery, pharmacy, psychology, nursing or allied health professions. Non-limiting examples of such users may include genetic counselors, clinicians, physicians, dentists, dental hygienists, pharmacists, pharmacy technicians, physician assistants, nurses, advanced practice registered nurses, surgeons, surgeon's assistant, athletic trainers, exercise physiologists, athletic trainers, surgical technologist, midwives, dietitians, nutritionists, therapists, chiropractors, social workers, phlebotomists, occupational therapists, optometrists, physical therapists, radiographers, radiotherapists, respiratory therapists, audiologists, speech pathologists, operating department practitioners, emergency medical technicians, paramedics, medical laboratory scientists, medical prosthetic technicians, naturopaths, combinations thereof, and/or the like. It is to be understood that while the users primarily referenced in the various examples in this disclosure relates to the healthcare field, users may also include personnel associated with other industries including, but not limited to, engineering, information technology (IT), aviation, retail, and/or the like.

As used herein, a "chat application" may refer to a computer-implementable software application for communication over a network (e.g., the Internet) that offers a real-time transmission of messages from a sender to a receiver. In some cases, the chat application may include a different interface for different users. For example, the chat application may have a different interface for patients versus clinicians. The different interfaces may allow for different types of information (e.g., medical records, videos, genetic test results, etc.) to be viewed and/or exchanged by the different users.

As used herein, "genetic data" may refer to personal data relating to the inherited or acquired genetic characteristics of a person which result from the analysis of a biological sample from the person. In particular, the genetic data may be obtained from a genetic test including a chromosomal, deoxyribonucleic acid (DNA) or ribonucleic acid (RNA) analysis, or from the analysis of another element enabling equivalent information to be obtained. In some examples, the genetic data may be viewed and/or exchanged by the users of the message exchange platform.

As used herein, a "genetic test" may refer to a medical test that allows the determination of bloodlines and the genetic diagnosis of vulnerabilities to inherited diseases. In particular, the genetic test may be administered by an entity and associated clinicians and/or physicians. Genetic testing may be used to diagnose or rule out a specific genetic or chromosomal condition. Genetic testing may be used to confirm a diagnosis when a particular condition is suspected based on physical mutations and symptoms. The results of a diagnostic test can influence a person's choices about health care and the management of the disease. In some examples, the genetic test results may be viewed and/or exchanged by the users of the message exchange platform.

As used herein, a "gene variant" (also referred to as a variant of uncertain or unknown significance, VUS) may refer to a allele, or variant form of a gene, which has been identified through genetic testing, but whose significance to the function or health of an organism is not known. Two related terms include gene of uncertain significance (GUS), which refers to a gene which has been identified through genome sequencing, but whose connection to a human disease has not been established. When the variant has no impact on health, the gene variant may be refer to as a benign variant. When the variant is associated with a disease, the gene variant may be called a pathogenic variant.

As used herein, "documents" may refer to academic work that is published in academic journal article, book or thesis form, academic publishing, a paper is an academic work that is usually published in an academic journal. Documents may contain original research results or may include reviews of existing results. Documents may include those articles that have undergone a process of peer review by one or more referees (who are academics in the same field) who check that the content of the paper is suitable for publication in the journal. In particular, the documents may include research results associated with particular genetic tests and/or gene variants. The documents may be used by the users to determine additional procedures for the patients to follow (e.g., additional genetic test to take, particular medications to take, etc.).

As used herein, a "machine learning algorithm" may refer to any suitable computer implementable technique that can build a mathematical model of sample data, known as training data, in order to make predictions or decisions without being explicitly programmed to perform the task. In some respects, machine learning tasks may be classified into several broad categories. In supervised learning, the algorithm may build a mathematical model from a set of data that contains both the inputs and the desired outputs. For example, if the task were determining whether an genetic test result contained a certain gene, the training data for a supervised learning algorithm would include other genetic test results with and without that gene (the input), and each genetic test results would have a label (the output) designating whether it contained the gene. Machine learning algorithms may include semi-supervised learning algorithms that develop mathematical models from incomplete training data, where a portion of the sample input does not have labels. Further, machine learning algorithms may include unsupervised learning algorithms, where the algorithm may build a mathematical model from a set of data which contains only inputs and no desired output labels. Unsupervised learning algorithms may be used to find structure in the data, like grouping or clustering of data points aw particular genes. Unsupervised learning can discover patterns in the data (e.g., genetic test results), and can group the inputs into categories (e.g., at-risk or not at-risk).

Embodiments of the disclosure present disclosure are generally directed to computer-based systems and methods for facilitating interactions between users (e.g., patients and clinicians) in a messaging exchange platform, the interactions including messages having queries. The management computing entity 100 may provide techniques for augmenting a communication, for example, by allowing a different user (e.g., another clinician) to review the messages and propose a response to a given query in the communication for which the user may choose to incorporate into the communication. Moreover, the management computing entity 100 may allow AI-based techniques to review repositories of chat information and suggest responses to queries that may be incorporated by the users into the communication. The system can further provide mechanisms for the user to modify suggested responses prior to transmission. This method allows one or more users to help generate responses, which the primary business or professional can incorporate in their chat conversation.

The management computing entity 100 may be configured to allow the responses to be used directly or to be edited by a user before transmission over the message exchange platform. Further, the responses may be presented alongside automatically-generated responses, and the user may incorporate features of the automatically-generated responses into their own response. Moreover, the management computing entity 100 may determine scores associated with the user-generated responses. Accordingly, only responses having a score above a certain threshold score may be exchanged on the message exchange platform. In some examples, the responses may include media files (e.g., videos and/or audio files).

FIG. 4 illustrates a flow diagram of an example, nonlimiting method that can facilitate human-augmented messaging, in accordance with example embodiments of the disclosure. At block 402, the method includes receiving a test (e.g., genetics test) result for a user. In some examples, the management computing entity 100 may receive the test result via an external device, for example, a third-party server (e.g, a cloud-based server). In another example, the management computing entity 100 may have one or more certificates that allow the management computing entity 100 to be preauthorized to receive the test results. In some examples, the management computing entity 100 may receive the test results in accordance with a health insurance portability and accountability act (HIPPA) protocol. In other examples, the management computing entity 100 may store the test results in a secure server or similar device. The management computing entity 100 may offer an interface where entities can provide the test results associated with the patient in a secure manner (e.g., via encryption).

At block 404, the method includes providing asynchronous communications (e.g., chat) channel between users such as a patient and a clinician. In some examples, the management computing entity 100 may implement a message exchange platform to provide the asynchronous communications channel. In some cases, the patient may initiate a communication (e.g., a chat message), and the clinician may not be available to answer immediately. Accordingly, the message exchange platform may retain the communication and present it to the clinician at a later time for asynchronous feedback. The management computing entity 100 may implement the asynchronous communications channel using any suitable software platform and any suitable network connection including, but not limited to, a wired and/or wireless network.

At block 406, the method includes retrieving information from chat and determining augmented feedback from other users (e.g., other clinicians) using AI-based algorithms. In some examples, retrieving information from the chat may include extracting keywords associated with messages provided by the patient. The keywords may then be used to search a database of previous responses to queries and/or any other suitable informational database. In some cases, based on the keywords, different clinicians from the clinician in communication with the user may be recruited and may be presented with the query in order for such different clinicians to contribute to the response to the query. The recruiting of the different clinicians may be based on a database storing credentials and user profiles associated with the clinicians. Further, the disclosed systems may search the database based on the keywords to determine the identities of the different clinicians. In some cases, AI-based techniques may be used to provide at least a partial response to the query. Further, the different clinicians may supplement or correct the AI-based response.

At block 408, the method includes sending a summary and/or recommendation to a requesting entity. In some cases, the summary may be based at least in part on the augmented feedback generated at block 406. In particular, the summary may include an abbreviated portion of a response to a query of a patient. Further the summary and/or recommendations may recap information pertaining to background information associated with the patient such as the patient's disease or other condition. In some cases, the requesting entity may include a hospital, a place of work, a legal institution, combinations thereof, and/or the like. The summary and/or recommendations may include specific instructions for a user to follow in order to manage and/or prevent the occurrence of an associated disease. In other cases, the summary and/or recommendation may include a prescription provided by a clinician. Further, such a prescription may be authorized by a doctor or any other suitable supervising authority.

FIG. 5 illustrates a block diagram of an example, non-limiting system for providing a human-augmented communications platform, in accordance with example embodiments of the disclosure. In particular, diagram 500 illustrates a system 501 (detailed below), a network 503, a server 505, user devices 507, and users 509. The system 501 may communicate over the network 503 to various user devices 507 and servers 505. The management computing entity 100 may use the servers 505 to store information and/or optimize data transmissions over the network 503. The user devices 507 may be configured to present and receive information (e.g., responses to queries) from users 509.

System 501 (and other systems described herein), apparatuses, or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

System 501 can optionally include a server device, one or more networks and one or more devices (not shown). The system 501 can also include or otherwise be associated with at least one processor 502 that executes computer executable components stored in memory 504. The system 501 can further include a system bus 506 that can couple various components including, but not limited to, a communications component 508, the message identification component 510, the recommendation component 512, and the scoring component 514, to be detailed below. The system 501 can be any suitable computing device or set of computing devices that can be communicatively coupled to devices, non-limiting examples of which can include, but are not limited to, a server computer, a computer, a mobile computer, a mainframe computer, an automated testing system, a network storage device, a communication device, a web server device, a network switching device, a network routing device, a gateway device, a network hub device, a network bridge device, a control system, or any other suitable computing device. A device can be any device that can communicate information with the system 501 and/or any other suitable device that can employ information provided by system 501. It is to be appreciated that system 501, components, models or devices can be equipped with communication component 512 that enable communication between the system, components, models, devices, etc. over one or more networks.

The system 501 may include various components (e.g., a communication component 508, a message identification component 510, a recommendation component 512, and a scoring component 514) that can perform operations for human augmentation of communications over a network. In particular, such operations may include, but not be limited to, identifying, via the message identification component 510, a message associated with a message exchange platform, the message including a query. In particular, the query may be provided by a patient. The patient may have an associated genetic test or other medical test result. The patient may wish to interact with various clinicians to obtain further information about their results of their test and may be using the message exchange platform to perform the interaction. The message identification component 510 may be configured to detect when a user begins interacting with the message exchange platform and may implement any suitable computer-implemented technique to determine the occurrence of a query. For example, the message identification component 510 may be configured to search for the occurrence of a question mark or similar symbol to determine the occurrence of a query during the ongoing communication between users.

The operations may further include causing to transmit, via a communication component 508, the message to users (e.g., clinicians) at respective user devices (e.g., mobile phones, laptops, tablets, and/or the like). The communication component 508 may include any suitable circuitry and/or transceiver to transmit the messages over a wired or wireless network to the user devices. In this way, the users may not necessarily need to be present at a particular device in order to receive the messages from the patients. Rather, such users may receive the messages at their personal devices (such as their mobile phones) allowing the users to respond under suitable circumstances.

The operations may further include receiving, via a recommendation component 512, responses to the query from the respective user devices. In particular, the recommendation component 512 may receive the responses from the user devices indicative of the clinician's answers to the patient's query. The recommendation component 512 may receive multiple answers over a period of time (e.g., a week). Accordingly, the recommendation component 512 may provide a configurable time threshold whereby the recommendation component 512 receives the answers and ultimately makes a recommendation of the best answer or composite answer to the patient.

The operations may further include determining, via a scoring component 514, respective scores of the responses. In particular, the scoring component 514 may be configured to determine respective response keywords associated with each of the responses. The scoring component 514 may identify, via the message identification component 510, at least one previously-generated response (e.g., a response generated by clinician to a similar query in the past). The scoring component 510 may then determine historical keywords from previously generated response, and may determine a number of matches between the response keywords and the historical keywords. The scoring component 514 may thereby determine the respective scores of the responses based on the number of matches. For example, the greater the number of matches, the higher the score of a given response.

In some examples, the scoring component 514 may identify entities associated with the responses and may determine the respective scores of the responses based on the entity. For example, a given entity generating a first response may include a relatively high-ranking hospital or research lab, while a different entity generating a second response may include a relatively lower ranking hospital or research lab. In such a case, the scoring component may weigh the respective scores of the different entities differently, associating a higher score with the first response from the high-ranking hospital research lab.

In some examples, the scoring component 514 may identify, via the message identification component 510, previously generated responses associated with the query from a database. The scoring component 514 may further identify respective previous scores associated with the previously generated responses. Such previous scores may have been determined by the scoring component 514 in the past. Then, the scoring component 514 may train a machine learning algorithm using the previous scores and the previously generated responses. Further, the scoring component 514 may determine, using the trained machine learning algorithm, the respective scores of the responses in the present. In this way, machine learning algorithms may be used to simulate the decision-making process executed by the scoring component in historical contexts.

The scoring component 514 may not solely rely upon AI-based techniques to determine the scores of the responses but may rather incorporate human judgments. In particular, the management computing entity 100 may receive a user input indicative of a user-assigned score for at least one of the responses, and the scoring component 514 may determine the respective scores based on the user input. In some examples, the management computing entity 100 may select, via the scoring component 514, at least one response having a score exceeding a predetermined threshold. The threshold may include a numerical threshold (e.g., a threshold of "8" on a scoring scale of 1 to 10).

In various embodiments, components of the system 501 (such as communications component 508, the message identification component 510, the recommendation component 512, and the scoring component 514) can include functional elements that can be implemented via cloud technologies, physical components (for example, computer hardware) and local software (for example, an application on a mobile phone or an electronic device).

The system 100 can include a communication component 508. The communication component 508 can be used for transferring data and facilitating the exchange of information between the different system components of the system 501 or between the system 501 and one or more external elements. In some embodiments, the communication component 512 can include internal storage, for example, memory. In some embodiments, the communication component 512 can serve to queue information between components and user device(s), such that the system operates in an efficient manner without excessive lag times. The communication component 512 can communicate information from a user interface, the information including, for example, suggested treatment options and user feedback. The communication component 512 can communicate with a cloud computing environment. The communication component can, for example, obtain information from the cloud computing environment related to pooled statistics for many users over a given geographical area from the cloud computing environment and can communicate this information to the computing component 510, for example, for use in the determination of responses to patient queries. For example, the pooled statistics may be used to train and improve machine-learning algorithms that generate AI-based responses.

Embodiments of devices described herein can employ AI to facilitate automating one or more features described herein. The components can employ various AI-based schemes for carrying out various embodiments/examples disclosed herein. To provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system, environment, etc. from a set of observations as captured via events and/or data. Determinations can be employed to identify a specific context or action, or can generate a probability distribution over states, for example. The determinations can be probabilistic—that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, etc.)) schemes and/or systems (e.g., support vector machines, neural networks, expert systems, Bayesian belief networks, fuzzy logic, data fusion engines, etc.) in connection with performing automatic and/or determined action in connection with the claimed subject matter. Thus, classification schemes and/or systems can be used to automatically learn and perform functions, actions, and/or determinations.

A classifier can map an input attribute vector, $z=(z1, z2, z3, z4, \ldots, zn)$, to a confidence that the input belongs to a class, as by $f(z)=confidence(class)$. Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence can be employed. Classification as used herein also is inclusive of statistical regression that is utilized to develop models of priority.

Figure 6A:
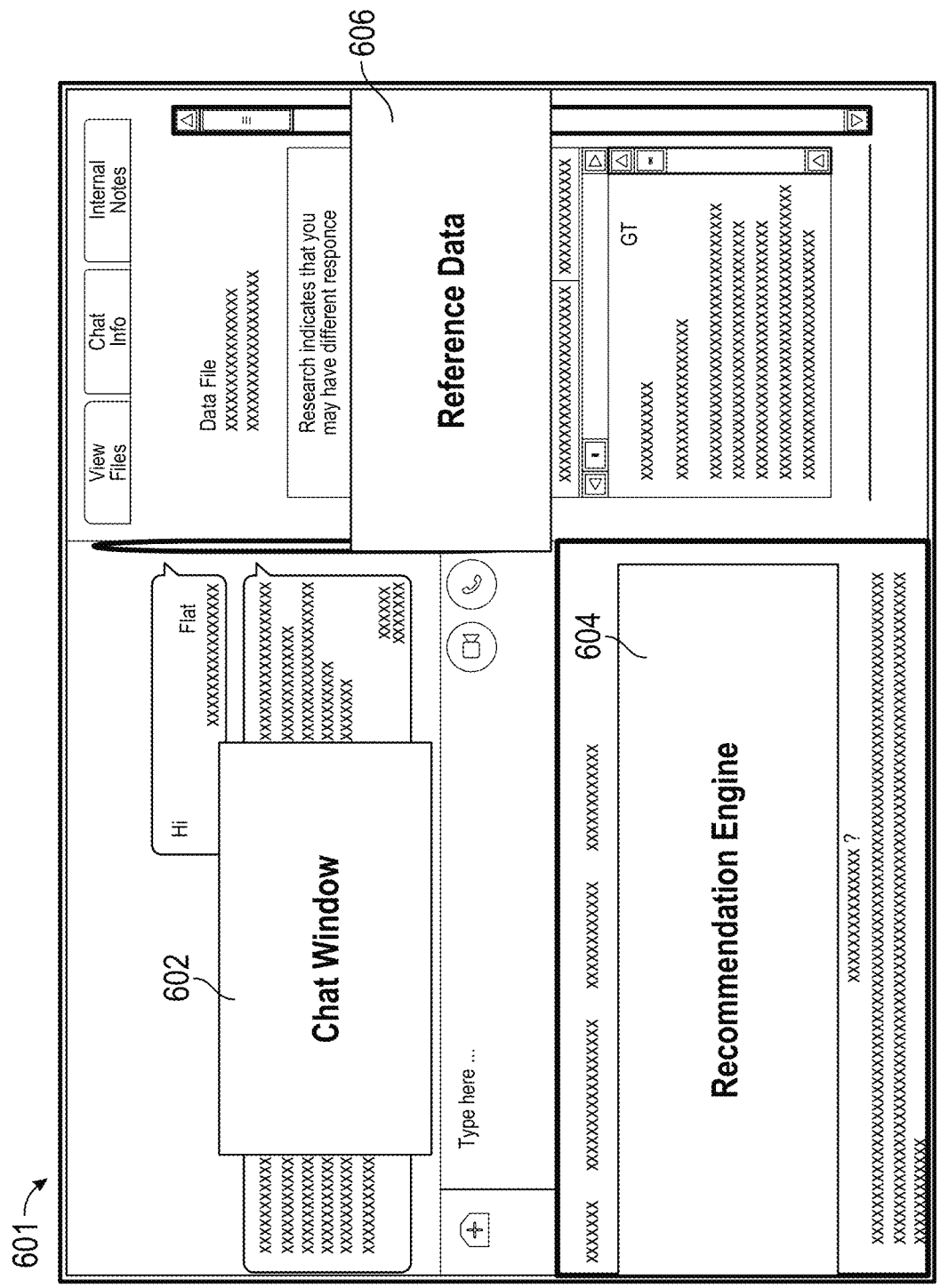

FIG. 6A illustrates a diagram representing partitions of a chat application, in accordance with example embodiments of the disclosure. In particular, diagram 601 represents a chat application having a chat window 602, a reference data 604, and a recommendation engine 604.

In some examples, the chat window 602 may represent a section of the chat application where patients and users interact using text-based messages in addition to audio, and/or video communications. In an example, the reference data 604 may represent a section of the chat application where pertinent information may be displayed to the users and/or the patients. For instance, the reference data 604 may include genetic test results, disease information associated with the genetic test results as mined from a database, related information as determined from the Internet, and/or the like. In some examples, the recommendation engine 604 may represent a section of the chat application where the management computing entity 100 may display a recommended response to the query. For example, the recommended response may include a user-augmented response based on responses generated from other clinicians. Additionally or alternatively, the recommended response may include an AI-based response as generated by a machine learning algorithm.

Figure 6B:
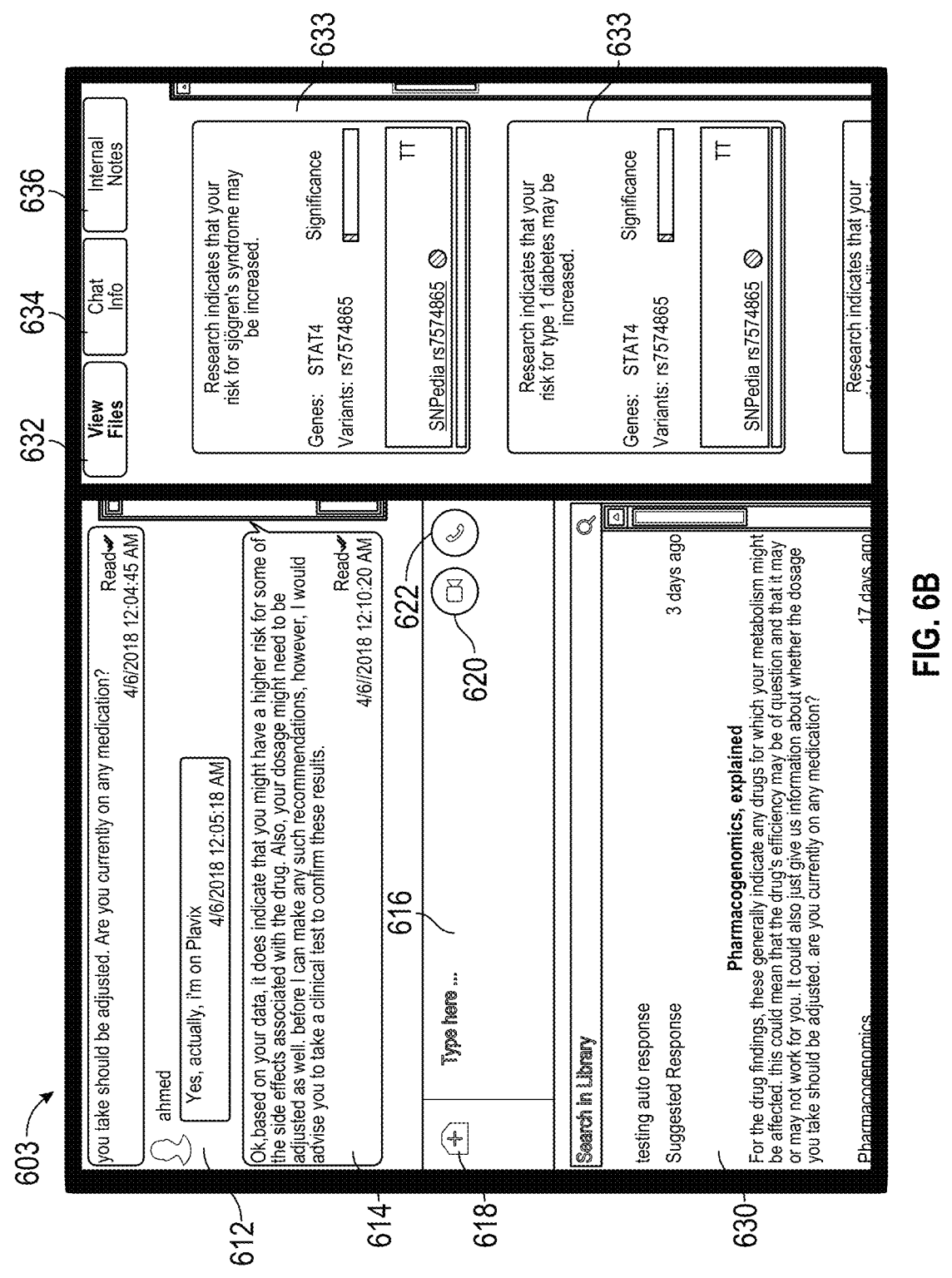

FIG. 6B illustrates a screenshot of the chat application, in accordance with example embodiments of the disclosure. In particular, diagram 603 illustrates a screenshot of the chat application from the perspective of a clinician. Further, diagram 603 illustrates various components including a patient communication 612, an entity communication 614, an entity communication box 616, an add photo option 618, a video communication option 620, an audio communication option 622, a suggested response 630, a view files option 632, a chat information option 634, an internal notes option 636, an example risk assessment notes 638, a patient communication 612, an entity communication 614, an entity communication box 616, an add photo option 618, a video communication option 620, an audio communication option 622, a suggested response 630, a view files option 632, a chat information option 634, an internal notes option 636, and an example risk assessment notes 633.

Patient communication 612 represents communication such as messages provided by a patient. The patient may interact with the chat application on a user device. The patient may, for example, input queries and other information to the chat application to send messages to the clinicians. In this example, the patient communication 612 shown indicates that the patient is on a particular drug (e.g., Plavix).

Entity communication 614 represents communications such as messages provided by a user (e.g., a clinician and/or a physician) associated with an entity. The user may, for example, input responses to the queries generated by the patient along with other pertinent information using the chat application. In this example the entity communication 614 shown indicates that the user believes that the patient has certain risks associated with taking the particular drug and suggests follow-up testing.

Entity communication box 616 represents an interface through which the user can provide a response to a query. For example, the user may type a response to the query. Besides merely typing a response, the management computing entity 100 also provide other options for the user to interact with the patient. For example, the chat application includes an add photo option 618 that allows the user to add a photo for transmission to the user. For example, the photo may include a photo associated with a given medical condition that the user may have. The chat application may also include a video communication option 620 that allows the user to add a video for transmission to the user. The video may include instructions or other information associated with the management of a condition that the patient may have. The chat application may also include an audio communication option 622 that allows the user to add an audio for transmission to the user. The audio may include instructions or other information associated with the management of a condition that the patient may have.

In some examples, the management computing entity 100 may generate an artificially-generated video for transmission to the patients using the video communication option 620, the artificially-generated video representing a user's face and/or body explaining instructions and/or other information associated with the management of the condition that the patient may have. In particular, the management computing entity 100 may receive at least one media file of a user, the media including a video of the user's face and audio of the user's voice. Further the management computing entity 100 may train a machine learning algorithm to mimic the user's face and the user's voice using the media file. Accordingly, the management computing entity 100 may generate an additional media file of the user, the additional media file including an additional video of the user's face and additional audio of the user's voice presenting the response. In some examples, the management computing entity 100 can transcribe audio from a conversation between users (e.g., a patient and a genetic counselor). The management computing entity 100 can then determine information (e.g., suggestions) to mention during the conversation, the information being generated using the transcribed audio and an AI-based technique. Further, the management computing entity 100 can send the suggested information to the users for presentation at the user devices. In this way, a given user (e.g., the genetic counselor) can provide augmented responses to another user's queries.

Suggested response 630 may represent a section of the chat application where AI-based responses and/or other user-augmented responses may be presented to the user for possible transmission to the patient. In particular, the management computing entity 100 may monitor the ongoing communication between the patient and the user, extract various keywords from the communication, and process the keywords to generate the suggested response to a patient query. As noted, the suggested response may be determined from a plurality of responses generated by other users also using the chat application. Such responses may be scored, via a scoring component, and the best response or a combination of responses may be presented as the suggested response. Further, the suggested response may be based on historical responses to similar queries. For example, the management computing entity 100 may identify, via a message identification component, previously generated responses associated with the query from a database, identify respective previous scores associated with the previously generated responses, and train a machine learning algorithm using the previous scores and the previously generated responses.

View files option 632 may represent a tab of the chat application whereby the user may view associated data files (e.g., test results, patient profile information, and/or the like). This may allow a user to gauge the context in which a response to a patient query is being made. Further the view files option 632 may streamline the process of viewing the patient's files without having to obtain them manually and or upload them individually from a hard disk.

In the screenshot shown in diagram 603, the view files option 632 is featured. In this case the view files option 632 includes example risk assessment notes 633 that indicate possible risk factors associated with a given patient's conditions. In particular, to generate such example risk assessment notes 633, the management computing entity 100 may identify genetic data associated with a patient, and determine, using an AI-based technique, one or more gene variants based on the genetic data. Further, the management computing entity 100 may determine, using the AI-based technique, documents associated with the gene variants. Such documents may include various research articles that are published via online databases. The management computing entity 100 may search such databases and perform operations such as text mining to determine the risk assessment notes 633.

Chat information option 634 may represent a tab of the chat application that includes information associated with the ongoing communications between the patient and the users. For example, the chat information option 634 may display the name of the individual(s) that are part of the communication, the time associated with the communication, various entities associated with the individuals, license information (e.g., medical licenses and other such authorizations), network configuration information, and/or the like.

Internal notes option 636 may represent a tab of the chat application that includes a record of various notes generated by a user during a communication with the patient. For example, the internal notes option 636 may include notes taken by the user indicative of a patient's condition, other associated factors and/or items to research, and/or information that the user wishes to share with other users that are viewing the communication with the patient. In various aspects the internal notes option 636 may represent a useful feature that allows other users to review the thought process of a given user in making a response to a patient query. This made enhance the quality of the disclosed system's responses to the user's query.

Figure 6C:
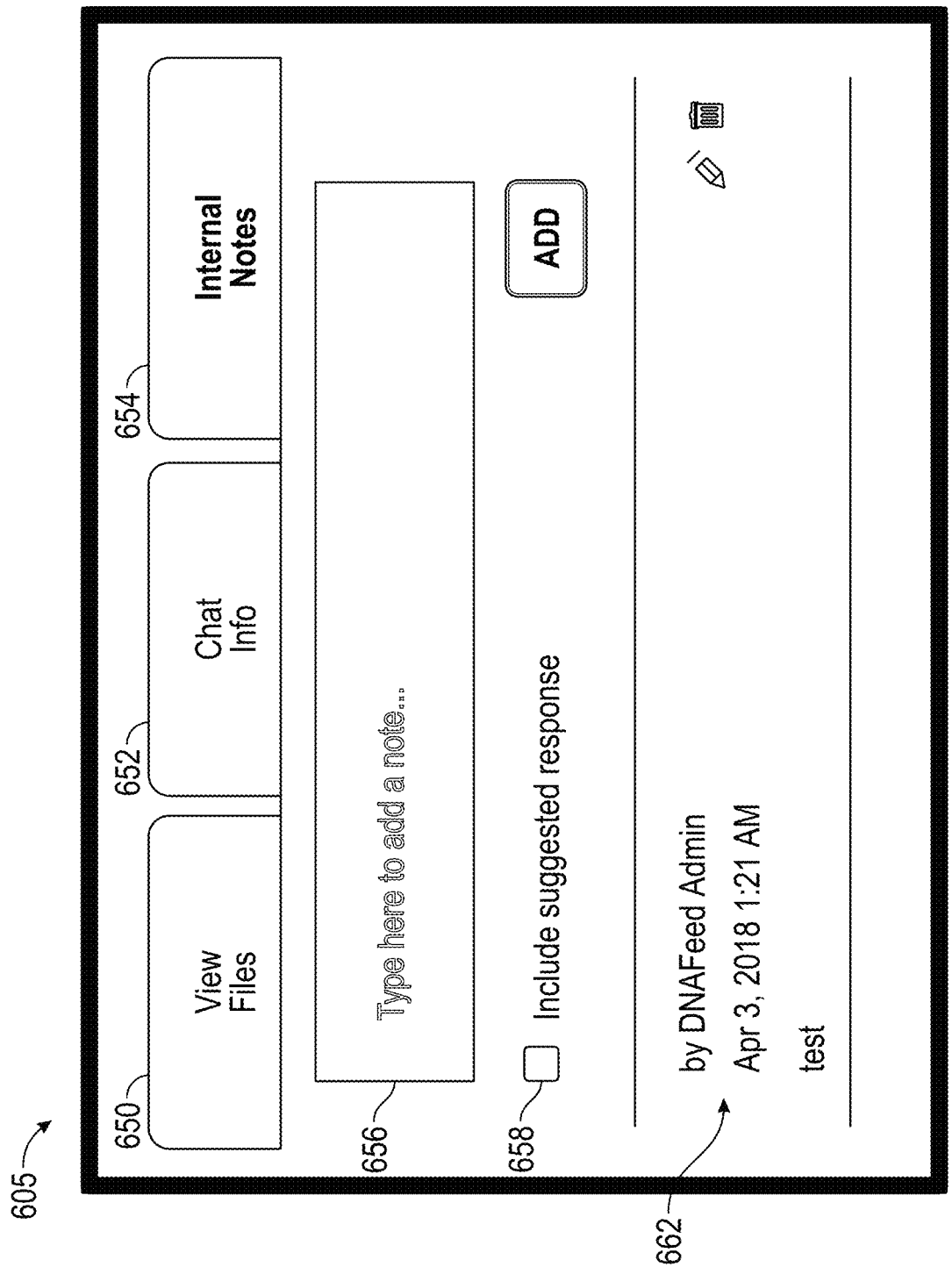

FIG. 6C illustrates another screenshot of the chat application, in accordance with example embodiments of the disclosure. Diagram 605 illustrates various components including a view files option 650, a chat information option 652, an internal notes option 654, an add note box 656, an include suggested response checkbox 658, and an identifying information 662.

View files option 650 may represent a tab of the chat application whereby the user may view associated data files (e.g., test results, patient profile information, and/or the like). The view files option 650 may be similar to view files option 632, described above.

Chat information option 652 may represent a tab of the chat application that includes information associated with the ongoing communications between the patient and the users. The chat information option 652 may be similar to the chat information option 634, described above.

Internal notes option 654 may represent a tab of the chat application that includes a record of various notes generated by a user during a communication with the patient. The internal notes option 654 may be similar to internal notes option 636, described above. Further, the internal notes option 654 may include an add note box 656, where the user may type a note. The internal notes option 654 may further feature an include suggested response checkbox 658, which allows the user to include suggested responses as variously described herein. The internal notes option 654 may include identifying information 662, that includes information related to the user's identity, the date and/or time, and an optional message.

Figure 6D:
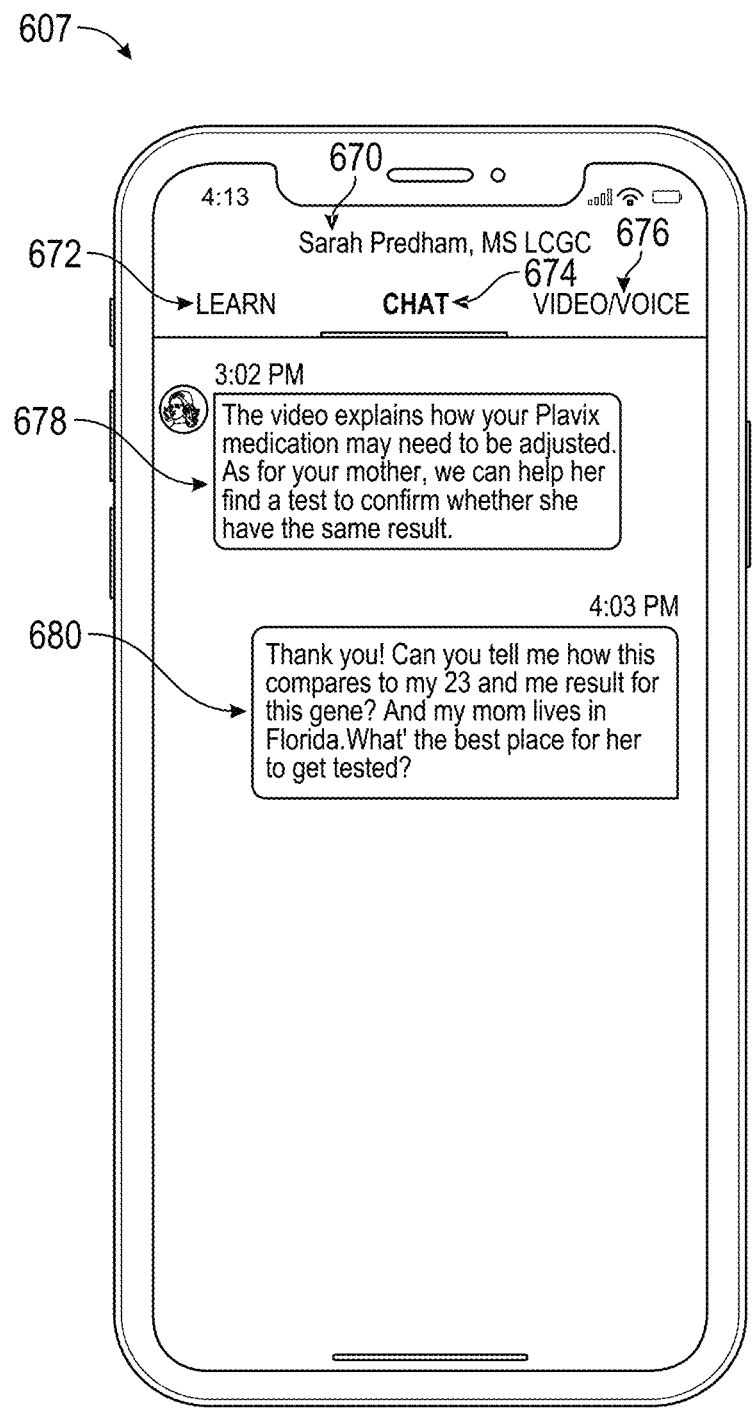

FIG. 6D illustrates another screenshot of the chat application, in accordance with example embodiments of the disclosure. In particular, diagram 607 shows a screenshot of an application on the patient's device representing interactions from the point of view of the patient.

Diagram 607 includes various components such as an entity identifier 670, a learn interaction area 672, a chat interaction area 674, a video/voice interaction area 676, an entity communication 678, and a patient communication 680. In some examples, the entity identifier 670 may serve to identify the clinician and/or physician that the patient is interacting with. In this example, the clinician is "Sarah Predham."

Learn interaction area 672 may represent a tab of the application, which may include information as provided by an administrator. For example, such information may include general information associated with using the application in addition to information related to the patient's condition. This may serve to reduce the time required by a clinician such as genetic counselor to complete the communication with the patient.

Chat interaction area 674 may represent an active area where the communication is performed between the patient and a user such as a clinician. In particular, the patient may type messages for transmission to the user. The chat interaction area 674 shows an exemplary entity communication 678. The entity communication 678 may include a message typed by a clinician for the patient. In this example, the entity communication 678 includes a message that describes how the clinician may need to adjust a patient's prescription. The entity communication 678 also describes how the clinician may proceed with treatments for a condition associated with the patient's mother. Further, in this example, the chat interaction area 674 may include a patient communication 680, which represents a message typed by a patient for the clinician. In particular, the patient communication 680 includes a query for the clinician related to how a particular test result compares with another test result from a third party. Further the patient communication 680 includes another follow-up question related to the user's mother.

Video/voice interaction area 676 may represent a section of the application where the patient may stream and/or record video and/or audio for transmission to the user(s). Moreover, the video/voice interaction area 676 may include a section of the application where the users (e.g., clinicians) provide recorded videos and/or audio files for the patient to view. For example, such recorded videos and/or audio files may represent instructions for the patient to follow to help the patient manage a medical condition.

One advantages of dividing the application into a learn interaction area 672 and a chat interaction area is that, by doing so, the management computing entity 100 may implement human-to-human augmentation. For instance, an administrator may handle many procedural and/or administrative questions by the patient while the clinician can focus on providing substantive responses to the user's medical queries. This can thereby allow the management computing entity 100 to make the genetic counseling process more efficient, and also simultaneously reduce computational loads on associated networks and devices.

FIG. 7 illustrates an exemplary method for performing the operations described herein, in accordance with example embodiments of the disclosure. At block 702, the method may include identifying at least one message associated with a message exchange platform, the message including a query. As noted, a message identification component may be configured to detect when a user begins interacting with the message exchange platform and may implement any suitable computer-implemented technique to determine the occurrence of a query. For example, the message identification component 510 may be configured to search for the occurrence of a question mark or similar symbol to determine the occurrence of a query.

At block 704, the method may include transmitting the message to one or more users at respective user devices. The transmission may be performed using a communication component that may include any suitable circuitry and/or transceiver to transmit the messages over a wired or wireless network to the user devices. In this way, the users may not necessarily need to be present at a particular device in order to receive the messages from the patients.

At block 706, the method may include receiving, via a recommendation component 512, responses to the query from the respective user devices. In particular, the recommendation component 512 may receive the responses from the user devices indicative of the clinicians' answers to the patient's query. The recommendation component 512 may receive multiple answers over a period of time (e.g., a week). Accordingly, the recommendation component 512 may provide a configurable time threshold whereby the recommendation component 512 receives the answers and ultimately makes a recommendation of the best answer or composite answer to the patient.

At block 708, the method may include determining respective scores of the responses. In particular, the scoring component 514 may configured to determine respective response keywords associated with each of the responses. The scoring component 514 may identify, via the message identification component 510, at least one previously-generated response (e.g., a response generated by clinician to a similar query in the past). The scoring component 510 may then determine historical keywords from previously generated response, and may determine a number of matches between the response keywords and the historical keywords. The scoring component 514 may thereby determine the respective scores of the responses based on the number of matches. For example, the greater the number of matches, the higher the score of a given response.

At block 710, the method may include selecting at least one response having a score exceeding a predetermined threshold. The disclosed systems may then present the response to the patient at a device.

To provide a context for the various embodiments of the disclosed subject matter, FIG. 8 as well as the following discussion are intended to provide a general description of a suitable environment in which the various embodiments of the disclosed subject matter can be implemented. FIG. 8 illustrates a block diagram of an example, non-limiting operating environment in which one or more embodiments described herein can be facilitated. Repetitive description of like elements employed in other embodiments described herein is omitted for sake of brevity. With reference to FIG. 8, a suitable operating environment 800 for implementing various embodiments of this disclosure can include a computer 812. The computer 812 can also include a processing component 814, a system memory 816, and a system bus 818. The system bus 818 can operably couple system components including, but not limited to, the system memory 816 to the processing component 814. The processing component 814 can be any of various available processors. Dual microprocessors and other multiprocessor architectures also can be employed as the processing component 814. The system bus 818 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 816 can also include volatile memory 820 and nonvolatile memory 822. The basic input/output system (BIOS), containing the basic routines to transfer information between elements within the computer 812, such as during start-up, can be stored in nonvolatile memory 822.

Computer 812 can also include removable/non-removable, volatile/non-volatile computer storage media. FIG. 8 illustrates, for example, a disk storage 824. Disk storage 824 can also include, but is not limited to, devices like a magnetic disk drive, floppy disk drive, tape drive, Jaz drive, Zip drive, LS-100 drive, flash memory card, or memory stick. The disk storage 824 also can include storage media separately or in combination with other storage media. To facilitate connection of the disk storage 824 to the system bus 818, a removable or non-removable interface can be used, such as interface 826.

FIG. 8 also depicts software that can act as an intermediary between users and the basic computer resources described in the suitable operating environment 800. Such software can also include, for example, an operating system 828. Operating system 828, which can be stored on disk storage 824, acts to control and allocate resources of the computer 812. System applications 830 can take advantage of the management of resources by operating system 828 through program components 832 and program data 834, e.g., stored either in system memory 816 or on disk storage 824. It is to be appreciated that this disclosure can be implemented with various operating systems or combinations of operating systems. A user enters commands or information into the computer 812 through one or more input devices 836. Input devices 835 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing component 814 through the system bus 818 via one or more interface ports 838. The one or more Interface ports 838 can include, for example, a serial port, a parallel port, a game port, and a universal serial bus (USB). One or more output devices 840 can use some of the same type of ports as input device 836. Thus, for example, a USB port can be used to provide input to computer 812, and to output information from computer 812 to an output device 840. Output adapter 842 can be provided to illustrate that there are some output devices 840 like monitors, speakers, and printers, among other output devices 840, which require special adapters. The output adapters 842 can include, by way of illustration and not limitation, video and sound cards that provide a means of connection between the output device 840 and the system bus 818. It should be noted that other devices and/or systems of devices provide both input and output capabilities such as one or more remote computers 844.

Computer 812 can operate in a networked environment using logical connections to one or more remote computers, such as remote computer 844. The remote computer 844 can be a computer, a server, a router, a network PC, a workstation, a microprocessor-based appliance, a peer device or other common network node and the like, and typically can also include many or all elements described relative to computer 812. For purposes of brevity, only a memory storage device 846 is illustrated with remote computer 844. Remote computer 844 can be logically connected to computer 812 through a network interface 848 and then physically connected via communication connection 850. Further, operation can be distributed across multiple (local and remote) systems. Network interface 848 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 850 refers to the hardware/software employed to connect the network interface 848 to the system bus 818. While communication connection 850 is shown for illustrative clarity inside computer 812, it can also be external to computer 812. The hardware/software for connection to the network interface 848 can also include, for exemplary purposes only, internal and external technologies such as, modems including regular telephone grade modems, cable modems and DSL modems, ISDN adapters, and Ethernet cards.

As mentioned herein, the systems, methods, and apparatuses described can be used in connection with cloud computing environments. Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows: Private cloud: the cloud infrastructure is operated solely for an organization. It may be managed by the organization or a third party and may exist on-premises or off-premises. Community cloud: the cloud infrastructure is shared by several organizations and supports a specific Community that has shared concerns (e.g., mission, security requirements, policy, and compliance considerations). It may be managed by the organizations or a third party and may exist on-premises or off-premises. Public cloud: the cloud infrastructure is made available to the general public or a large industry group and is owned by an organization selling cloud services. Hybrid cloud: the cloud infrastructure is a composition of two or more clouds (private, community, or public) that remain unique entities but are bound together by standardized or proprietary technology that enables data and application portability (e.g., cloud bursting for load-balancing between clouds). A cloud computing environment is service oriented with a focus on statelessness, low coupling, modularity, and semantic interoperability. At the heart of cloud computing is an infrastructure that includes a network of interconnected nodes.

Referring now to FIG. 9, an illustrative cloud computing environment 950 is depicted. As shown, cloud computing environment 950 includes one or more cloud computing nodes 910 with which local computing devices used by cloud consumers, such as, for example, personal digital assistant (PDA) or cellular telephone 954A, desktop computer 954B, laptop computer 954C, and/or automobile computer system 954N may communicate. Nodes 910 may communicate with one another. They may be grouped (not shown) physically or virtually, in one or more networks, such as Private, Community, Public, or Hybrid clouds as described hereinabove, or a combination thereof. This allows cloud computing environment 950 to offer infrastructure, platforms and/or software as services for which a cloud consumer does not need to maintain resources on a local computing device. It is understood that the types of computing devices 954A-N shown in FIG. 9 are intended to be illustrative only and that computing nodes 910 and cloud computing environment 950 can communicate with any type of computerized device over any type of network and/or network addressable connection (e.g., using a web browser).

IV. Additional Implementation Details

Although an example processing system has been described above, implementations of the subject matter and the functional operations described herein can be implemented in other types of digital electronic circuitry, or in computer software, firmware, or hardware, including the structures disclosed in this specification and their structural equivalents, or in combinations of one or more of them.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more modules of computer program instructions, encoded on computer storage medium for execution by, or to control the operation of, information/data processing apparatus. Alternatively, or in addition, the program instructions can be encoded on an artificially-generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or information/data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input information/data and generating output. Processors suitable for the execution of a computer program include, by way of example, both general and special purpose microprocessors, and any one or more processors of any kind of digital computer. Generally, a processor will receive instructions and information/data from a read-only memory or a random access memory or both. The essential elements of a computer are a processor for performing actions in accordance with instructions and one or more memory devices for storing instructions and data. Generally, a computer will also include, or be operatively coupled to receive information/data from or transfer information/data to, or both, one or more mass storage devices for storing data, e.g., magnetic, magneto-optical disks, or optical disks. However, a computer need not have such devices. Devices suitable for storing computer program instructions and information/data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (cathode ray tube) or LCD (liquid crystal display) monitor, for displaying information/data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described herein can be implemented in a computing system that includes a back-end component, e.g., as an information/data server, or that includes a middleware component, e.g., an application server, or that includes a front-end component, e.g., a client computer having a graphical user interface or a web browser through which a user can interact with an implementation of the subject matter described herein, or any combination of one or more such back-end, middleware, or front-end components. The components of the system can be interconnected by any form or medium of digital information/data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits information/data (e.g., an HTML page) to a client device (e.g., for purposes of displaying information/data to and receiving user input from a user interacting with the client device). Information/data generated at the client device (e.g., a result of the user interaction) can be received from the client device at the server.

While this specification contains many specific implementation details, these should not be construed as limitations on the scope of any embodiment or of what may be claimed, but rather as descriptions of features specific to particular embodiments. Certain features that are described herein in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

V. Conclusion

Many modifications and other embodiments of the disclosure set forth herein will come to mind to one skilled in the art to which these embodiments pertain having the benefit of the teachings presented in the foregoing descriptions and the associated drawings. Therefore, it is to be understood that the embodiments are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A device for human-to-human augmentation, comprising:
at least one memory device that stores computer-executable instructions; and
at least one processor configured to access the memory device, wherein the processor is configured to execute the computer-executable instructions to:
identify, via a message identification component, at least one message associated with a message exchange platform, the message including a query from a patient;
identify genetic data associated with the patient;
determine, using an AI-based technique, one or more gene variants based on the genetic data;
determine, using the AI-based technique, one or more documents associated with the gene variants;
cause to transmit, via a communication component, information associated with at least one of the gene variants and the documents to one or more personnel users at respective user devices;
cause to transmit, via the communication component, the message to the one or more personnel users at the respective user devices using encryption in accordance with a health-based protocol;
receive, via a recommendation component, responses to the query from the respective user devices from a first personnel user, and wherein the responses comprise at least one of a user-generated response by the first personnel user and a user-augmented response by the first personnel user;
receive, via a scoring component, a user input from a second personnel user indicative of a user-assigned score for at least one of the responses received from the first personnel user;
determine, via the scoring component, respective scores based on the user input from the second personnel user; and
select, via the scoring component, at least one response to be sent to the patient having a score exceeding a predetermined threshold.

2. The device of claim 1, wherein the responses are selected from the group consisting of a text file, an audio file, and a video file.

3. The device of claim 1, wherein the processor is further configured to execute the computer-executable instructions to:
determine, via the recommendation component, at least one artificial intelligence (AI) based response to the query using the AI-based technique;
cause to transmit, via the communication component, the AI-based response to the personnel users at the respective user devices; and
receive, via the recommendation component, the responses to the query from the respective user devices based on the AI-based response.

4. The device of claim 3, wherein the computer-executable instructions to determine the AI-based response further comprise computer-executable instructions to:
identify, via the message identification component, from a database of previously generated responses associated with the query, at least one previously generated response; and
input the previously generated response to the AI-based technique.

5. The device of claim 1, wherein the computer-executable instructions to determine, via the scoring component, the respective scores of the responses comprises computer-executable instructions to:
determine respective response keywords associated with each of the responses;
identify, via the message identification component, at least one previously generated response;
determine historical keywords previously generated response;
determine a number of matches between the response keywords and the historical keywords; and
determine the respective scores of the responses based on the number of matches.

6. The device of claim 1, wherein the computer-executable instructions to determine, via the scoring component, the respective scores of the responses comprises computer-executable instructions to:
identify entities associated with the responses; and determine the respective scores of the responses based on the entity.

7. The device of claim 1, wherein the computer-executable instructions to determine, via the scoring component, the respective scores of the responses comprises computer-executable instructions to:
   identify, via the message identification component, previously generated responses associated with the query from a database;
   identify respective previous scores associated with the previously generated responses;
   train a machine learning algorithm using the previous scores and the previously generated responses; and
   determine, using the trained machine learning algorithm, the respective scores of the responses.

8. The device of claim 1, wherein the computer-executable instructions to determine, via the scoring component, the respective scores of the responses comprises computer-executable instructions to:
   receive a user input indicative of a user-assigned score for at least one of the responses; and
   determine the respective scores based on the user input.

9. The device of claim 1, wherein the processor is further configured to execute the computer-executable instructions to cause to present the selected response via a chat application at a user device.

10. The device of claim 9, wherein the chat application comprises a graphical user interface (GUI) including a first interaction area for a first user of the one or more personnel users to input communications and a second interaction area for a second user of the one or more personnel users to input different communications.

11. The device of claim 1, wherein the processor is further configured to execute the computer-executable instructions to:
   receive at least one media file of a user of the one or more personnel users, the media including an audio of the user's voice;
   training a machine learning algorithm to mimic the user's voice using the media file; and
   generating an additional media file of the user, the additional media file including an additional audio of the user's voice presenting the response.

12. The device of claim 1, wherein the processor is further configured to execute the computer-executable instructions to:
   transcribe audio from a conversation between at least two users of the one or more personnel users;
   determine, via the recommendation component, at least one suggested information based on the transcribed audio using an AI-based technique; and
   cause to transmit, via the communication component, the suggested information to the personnel users at the respective user devices.

13. A system for human-to-human augmentation, comprising:
   at least one memory device that stores computer-executable instructions; and
   at least one processor configured to access the memory device, wherein the processor is configured to execute the computer-executable instructions to:
      identify, via a message identification component, at least one message associated with a message exchange platform, the message including a query from a patient;
      identify genetic data associated with the patient;
      determine, using an AI-based technique, one or more gene variants based on the genetic data;
      determine, using the AI-based technique, one or more documents associated with the gene variants;
      cause to transmit, via a communication component, information associated with at least one of the gene variants and the documents to one or more personnel users at respective user devices;
      cause to transmit, via the communication component, the message to the one or more personnel users at the respective user devices using encryption in accordance with a health-based protocol;
      receive, via a recommendation component, responses to the query from the respective user devices from a first personnel user, and wherein the responses comprise at least one of a user-generated response by the first personnel user and a user-augmented response by the first personnel user;
      receive, via a scoring component, a user input from a second personnel user indicative of a user-assigned score for at least one of the responses received from the first personnel user;
      determine, via the scoring component, respective scores based on the user input from the second personnel user; and
      select, via the scoring component, at least one response to be sent to the patient having a score exceeding a predetermined threshold.

14. The system of claim 13, wherein the processor is further configured to execute the computer-executable instructions to:
   determine, via the recommendation component, at least one artificial intelligence (AI) based response to the query using the AI-based technique;
   cause to transmit, via the communication component, the AI-based response to the personnel users at the respective user devices; and
   receive, via the recommendation component, the responses to the query from the respective user devices based on the AI-based response.

15. The system of claim 14, wherein the computer-executable instructions to determine the AI-based response further comprise computer-executable instructions to:
   identify, via the message identification component, from a database of previously generated responses associated with the query, at least one previously generated response; and
   input the previously generated response to the AI-based technique.

16. The system of claim 13, wherein the computer-executable instructions to determine, via the scoring component, the respective scores of the responses comprises computer-executable instructions to:
   determine respective response keywords associated with each of the responses;
   identify, via the message identification component, at least one previously generated response;
   determine historical keywords previously generated response;
   determine a number of matches between the response keywords and the historical keywords; and
   determine the respective scores of the responses based on the number of matches.

17. A computer-implemented method for human-to-human augmentation, comprising:

identifying, via a message identification component, at least one message associated with a message exchange platform, the message including a query from a patient;

identifying genetic data associated with the patient determining, using an AI-based technique, one or more gene variants based on the genetic data;

determining, using the AI-based technique, one or more documents associated with the gene variants;

transmitting, via a communication component, information associated with at least one of the gene variants and the documents to one or more personnel users at respective user devices;

transmitting, via the communication component, the message to the one or more personnel users at the respective user devices using encryption in accordance with a health-based protocol;

receiving, via a recommendation component, responses to the query from the respective user devices from a first personnel user, and wherein the responses comprise at least one of a user-generated response by the first personnel user and a user-augmented response by the first personnel user;

receive, via a scoring component, a user input from a second personnel user indicative of a user-assigned score for at least one of the responses received from the first personnel user;

determine, via the scoring component, respective scores based on the user input from the second personnel user; and select, via the scoring component, at least one response to be sent to the patient having a score exceeding a predetermined threshold.

18. The computer-implemented method of claim 17, further comprising:

determining, via the recommendation component, at least one artificial intelligence (AI) based response to the query using the AI-based technique;

transmitting, via the communication component, the AI-based response to the personnel users at the respective user devices; and receiving, via the recommendation component, the responses to the query from the respective user devices based on the AI-based response.

19. The computer-implemented method of claim 17, further comprising:

identifying, via the message identification component, from a database of previously generated responses associated with the query, at least one previously generated response; and inputting the previously generated response to the AI-based technique.

* * * * *